United States Patent [19]

Charbonneau

[11] 4,035,431

[45] July 12, 1977

[54] ALKYLENE-LINKED AROMATIC COMPOUNDS

[75] Inventor: Larry F. Charbonneau, Rochester, Mich.

[73] Assignee: General Motors Corporation, Detroit, Mich.

[21] Appl. No.: 616,958

[22] Filed: Sept. 26, 1975

[51] Int. Cl.² .......................................... C07C 15/12
[52] U.S. Cl. ......................... 260/668 C; 260/668 R
[58] Field of Search ....... 260/671 B, 668 C, 669 B, 260/668 R

[56] References Cited

U.S. PATENT DOCUMENTS

| | | | |
|---|---|---|---|
| 2,712,543 | 7/1955 | Greshem et al. | 260/346.3 |
| 3,441,625 | 4/1969 | Bargeron et al. | 260/668 C X |
| 3,649,601 | 3/1972 | Critchley et al. | 260/78 TF |
| 3,832,322 | 8/1974 | Critchley et al. | 260/37 N |
| 3,833,680 | 9/1974 | Torii | 260/668 R X |

OTHER PUBLICATIONS

Reuvers et al., CA 71:123335m, (1969).

*Physical Constants of Hydrocarbons*, vol. III, Egloff, ed., pp. 381, 383, 387, Reinhold Publishing, (1946).

*Primary Examiner*—Daniel E. Wyman
*Assistant Examiner*—Thomas A. Waltz
*Attorney, Agent, or Firm*—Jack I. Pulley

[57] ABSTRACT

In accordance with a preferred embodiment of this invention, an alkylene-linked dixylyl compound having the following structural formula is synthesized,

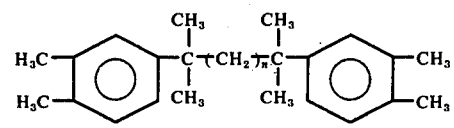

wherein $n$ may vary from 3 to 18. These compounds may be readily oxidized and dehydrated to form the corresponding alkylene-linked dianhydride which is useful as a precursor in the formation of alkylene-linked polyimide compounds and as a cross-linking or hardening agent in many curable polymer systems such as the epoxy resins.

2 Claims, No Drawings

ALKYLENE-LINKED AROMATIC COMPOUNDS

FIELD OF THE INVENTION

This invention is concerned with the synthesis of linked aromatic compounds through an electrophilic substitution type reaction mechanism.

BACKGROUND OF THE INVENTION

There is an ever increasing demand for easily processed thermoplastic resins which are thermally stable at higher and higher temperatures. Recent developments have produced many heavily aromatic compounds having the desired thermostability but lacking the desired processibility.

A key in developing a thermally stable and melt processible resin is maintaining adaquate flexibility along the polymer chain. The efforts which produced the subject invention were directed toward the general goal of synthesizing a polyimide precursor which would react with conventional diamine-terminated type compounds to form alkylene-linked polyimide resins. Therefore, it is an object of this invention to provide an alkylene-linked aromatic dixylyl compound which may be readily oxidized and dehydrated to form the corresponding dianhydride, which in turn will react with the aforementioned amine type compounds to form a thermally stable and yet easily processed polyimide resin.

It is a further object of this invention to provide a method of synthesizing an alkylene-linked dixylyl compound at relatively high yields by limiting the rates of the several competing reactions which may occur during the electrophilic substitution reaction.

SUMMARY OF THE INVENTION

In accordance with a preferred embodiment of this invention, an alkylene-linked dixylyl compound having the following structural formula

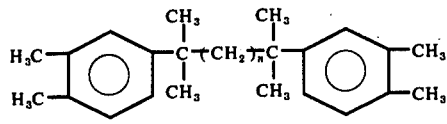

wherein $n$ may vary from 3 to 18, is synthesized from o-xylene and a ditertiary alcohol. Experimental work has shown that the addition of the alcohol to a mixture of ferric chloride and an excess of o-xylene at about 0° C. produces the desired alkylene-linked dixylyl at a yield of about 64%. In this reaction the ferric chloride and o-xylene mixture serve as the reacting medium; however, a solvent medium such as methylene chloride or nitrobenzene may also be used.

This type of reaction is often called a Friedel-Crafts reaction or, more generally, an electrophilic aromatic substitution. In this type of reaction, a hydroxyl group, which is bonded to one of the reactants, is activated by a suitable catalyst and a carbonium ion is apparently formed. This active ion then reacts with an aromatic ring of the other reactant and bonds the reactant initially containing the hydroxyl group directly to the aromatic ring. In preparing the subject compounds this type of bonding reaction must occur twice to form each alkylene-linked dixylyl molecule.

DETAILED DESCRIPTION OF THE INVENTION

In accordance with the practice of this invention, a ditertiary alcohol is twice reacted and covalently bonded to an aromatic compound forming an alkylene-linked aromatic compound which may be readily oxidized and dehydrated to form a dianhydride. This reaction is illustrated below:

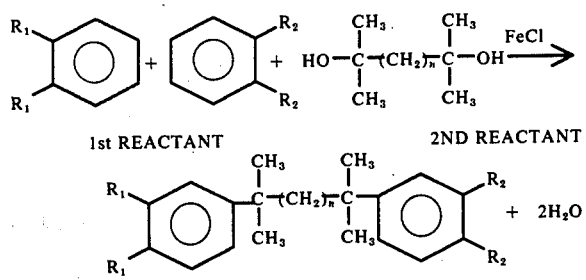

wherein $R_1$ and $R_2$ may be selected from the class consisting of methyl, ethyl, isopropyl but not necessarily the same and wherein $n$ may vary from 3 to 18.

In this reaction, a metal halide or an acid catalyst activates the tertiary alcohol groups of the second reactant which then reacts with the aromatic ring of the first reactant. This reaction covalently bonds the two reactants and splits off water as shown above. It is to be noted that a ditertiary halide could be substituted for the ditertiary alcohol as the second reactant.

As described in Basic Principles of Organic Chemistry by John D. Roberts and Majorie C. Caseiero, published by W. A. Benjamin Incorporated of New York in 1955 on page 794, the usefulness of this type of Friedel-Crafts reaction, often referred to as alkylation, is limited by several factors. In general, these factors may be described as side reactions competing with the basic substitution reaction. The first problem is that it is often difficult to limit the reaction to monosubstitution because the introduction of one alkyl substituent on the ring tends to activate it and promote a second substitution.

A second limitation of the usefulness of this type of reaction is its tendency to also produce rearrangement products. As an example, the authors of the aforementioned text cite that the alkylation of benzene with n-propylchloride leads to a mixture of n-propyl benzene and isopropyl benzene. In the subject synthesis such a rearrangement would not provide an acceptable result. Finally, the tendency of the alkylation products to isomerize and disproportionate is also cited, especially in the presence of large amounts of catalysts. Again, this type of reaction would not provide an acceptable product. These three limits on the usefulness of the subject alkylation reaction may be classed as competing reactions, the products of which must be minimized to provide reasonable yields of the desired alkylene-linked aromatic compounds.

As shown in the following example, a reasonable yield, of about 64%, may be obtained by using a relatively mild metal halide catalyst such as ferric chloride ($FeCl_3$) dissolved in an excess of the aromatic compound as the reaction medium and a reaction temperature of about 0° C.

It is to be noted that many typical Friedel-Crafts type catalysts were tested and proved effective in the subject reaction but produced varying yields. This list of catalysts includes: aluminum chloride ($AlCl_3$), hydrofluoric acid (HF), stannous chloride ($SNCl_4$) and boron trifluoride ($BF_3$). The yields of the reactions catalyzed by these halides varied from about 7% to about 24%: however, it is believed that these yields could be increased considerably by adjusting the reaction parameters.

EXAMPLE I

Herein, synthesis of certain compounds in the subject alkylene-linked dixylyl class will be detailed.

A one liter resin kettle was fitted with a stirrer, a condenser, and a solids addition flask. Then, 500 grams of o-xylene was added and the kettle was cooled to 0° C. Ferric chloride (200 g) was added over a 30 minute period, and then a slush of 30 g 2,7-dimethyl-2,7-octanediol in 50 ml of o-xylene was added over a two hour period while the reaction temperature remained at 0° C. After stirring for an additional 4 hours, the mixture was allowed to warm to room temperature, and was then poured onto ice. After separating the organic and aqueous layers, the organic layer was washed with water, and the solvent was removed from the organic layer. The crude black solid product was dissolved in boiling 95% ethanol and repeatedly passed through a pad of activated charcoal and Fuller's earth until a colorless solution was obtained. The yield was 64% and the white crystals from 95% ethanol melt at 68°–69° C.

EXAMPLE II

In accordance with the procedures set forth in Example I, 2,11-bis-(3,4-dimethyl phenyl)-2,11-dodecane was prepared. The quantities used were 40 g FeCl$_3$, 200 g-o-xylene, and 15 grams of 2,11-dimethyl-2,11-dodecane diol. A 30% yield of crystals were obtained from the ethanol solvent; the crystals had a melting point of about 61° C.

The compounds produced in accordance with the practice of this invention may be readily oxidized to form the tetracarboxylic acid and then dehydrated to form an alkylene-linked dianhydride.

While our invention has been described in terms of certain specific embodiments, it will be appreciated that other forms thereof could readily be adapted by one skilled in the art. Therefore, the scope of our invention is not to be limited to the specific embodiments disclosed.

I claim:

1. An alkylene-linked aromatic hydrocarbon compound which may readily be oxidized and dehydrated to form the corresponding dianhydride, said aromatic having the following structural formula:

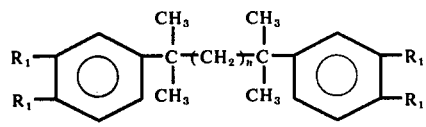

wherein $R_1$ is selected from the class consisting of —CH$_3$, —CH$_2$CH$_3$, CH$_3$—CH—CH$_3$ and $n$ may vary from 3 to 18.

2. An alkylene-linked dixylyl compound having the following structural formula:

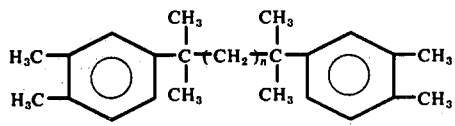

wherein $n$ may vary from 3 to 18.

* * * * *